US012706317B2

(12) United States Patent
Fuchs

(10) Patent No.: US 12,706,317 B2
(45) Date of Patent: Aug. 11, 2026

(54) SENSOR FOR DETECTING AT LEAST ONE PROPERTY OF A FLUID MEDIUM IN AT LEAST ONE MEASURING CHAMBER

(71) Applicant: Robert Bosch GmbH, Stuttgart (DE)

(72) Inventor: Tino Fuchs, Tuebingen (DE)

(73) Assignee: Robert Bosch GmbH, Stuttgart (DE)

( * ) Notice: Subject to any disclaimer, the term of this patent is extended or adjusted under 35 U.S.C. 154(b) by 348 days.

(21) Appl. No.: 18/044,810

(22) PCT Filed: Aug. 6, 2021

(86) PCT No.: PCT/EP2021/072035
§ 371 (c)(1),
(2) Date: Mar. 10, 2023

(87) PCT Pub. No.: WO2022/063476
PCT Pub. Date: Mar. 31, 2022

(65) Prior Publication Data
US 2023/0361325 A1 Nov. 9, 2023

(30) Foreign Application Priority Data
Sep. 23, 2020 (DE) ..................... 10 2020 211 893.0

(51) Int. Cl.
*G01N 27/18* (2006.01)
*G01N 33/00* (2006.01)
*H01M 8/0444* (2016.01)

(52) U.S. Cl.
CPC .......... *H01M 8/0444* (2013.01); *G01N 27/18* (2013.01); *G01N 33/0032* (2013.01); *G01N 33/005* (2013.01)

(58) Field of Classification Search
CPC ............. H01M 8/0444; H01M 8/0432; H01M 8/0438; G01N 27/18; G01N 33/0032; G01N 33/005; Y02E 60/50
See application file for complete search history.

(56) References Cited

U.S. PATENT DOCUMENTS 3,864,628 A * 2/1975 Klass .................. G01N 33/005 73/31.06
8,493,223 B2 * 7/2013 Zadnikar .......... G08B 13/19697 356/213

(Continued)

FOREIGN PATENT DOCUMENTS

EP 1621882 A2 2/2006
EP 3540420 A1 9/2019

(Continued)

OTHER PUBLICATIONS

International Search Report for PCT/EP2021/072035, Issued Nov. 19, 2021.

(Continued)

*Primary Examiner* — David J Bolduc
(74) *Attorney, Agent, or Firm* — Norton Rose Fulbright US LLP

(57) ABSTRACT

A sensor for detecting at least one property of a fluid medium in at least one measuring chamber, for detecting an $H_2$ fraction in a measuring gas. The sensor includes at least a first sensor element to detect a heat conductivity of the fluid medium and output a first measuring signal, a second sensor element including a semiconducting metal oxide and designed to output a second measuring signal, a third sensor element for detecting a physical property of the fluid medium, the third sensor element differing from the first sensor element and the second sensor element with regard to the detected physical property and being designed to output a third measuring signal, and an electronic evaluation unit for evaluating the first, second, and third measuring signal. The electronic evaluation unit is designed to change operating parameters of the first and/or second and/or third sensor element.

8 Claims, 1 Drawing Sheet

(56) References Cited

U.S. PATENT DOCUMENTS

| | | | | |
|---|---|---|---|---|
| 2002/0152037 | A1* | 10/2002 | Sunshine | G01N 33/0032 702/22 |
| 2002/0181501 | A1* | 12/2002 | Nova | G08B 25/003 370/467 |
| 2004/0181346 | A1* | 9/2004 | Sunshine | H04L 9/40 702/22 |
| 2011/0015875 | A1* | 1/2011 | Walte | G01N 27/622 250/286 |
| 2012/0247191 | A1* | 10/2012 | Herz | G01N 33/005 73/61.43 |
| 2013/0311108 | A1 | 11/2013 | Stetter et al. | |
| 2015/0276655 | A1* | 10/2015 | Henshaw | G01N 27/14 205/785.5 |
| 2016/0231303 | A1* | 8/2016 | Park | G01N 27/4045 |
| 2018/0052124 | A1* | 2/2018 | Rogers | G01N 27/18 |
| 2018/0321209 | A1* | 11/2018 | Gutierrez Martinez | G01N 33/18 |
| 2020/0033280 | A1* | 1/2020 | Kim | G08C 17/02 |
| 2021/0003525 | A1* | 1/2021 | Kaita | G01N 33/006 |
| 2021/0104140 | A1* | 4/2021 | Park | G08B 25/10 |
| 2021/0123876 | A1* | 4/2021 | Carr | G01N 27/18 |
| 2022/0107285 | A1* | 4/2022 | Tanabe | G01N 27/18 |
| 2022/0341864 | A1* | 10/2022 | Nojiri | G01N 27/18 |

FOREIGN PATENT DOCUMENTS

| | | | |
|---|---|---|---|
| JP | S5540424 | Y1 | 9/1980 |
| JP | H0682407 | A | 3/1994 |
| JP | H06102217 | A | 4/1994 |
| JP | H06130017 | A | 5/1994 |
| JP | 2007327926 | A | 12/2007 |
| JP | 2018004593 | A | 1/2018 |
| JP | 2018194409 | A | 12/2018 |
| JP | 2020030137 | A | 2/2020 |
| WO | 0054237 | A1 | 9/2000 |

OTHER PUBLICATIONS

Boon-Brett et al., "Identifying Performance Gaps in Hydrogen Safety Sensor Technology for Automotive and Stationary Applications," International Journal of Hydrogen Energy, Elsevier, vol. 35, No. 1, 2010, pp. 373-384. <http://lib.ysu.am/articles_art/5a3d82ec24dd710f2d1f62ad3a88ba92.pdf> Downloaded Mar. 9, 2023.

Hubert et al., "Hydrogen Sensors—a Review," Sensors and Actuators B: Chemical, Elsevier, vol. 157, No. 2, 2011, pp. 329-352.

* cited by examiner

SENSOR FOR DETECTING AT LEAST ONE PROPERTY OF A FLUID MEDIUM IN AT LEAST ONE MEASURING CHAMBER

BACKGROUND INFORMATION

Numerous sensors, sensor elements, and methods for detecting at least one property of a fluid medium in a measuring chamber are available in the related art. This may basically involve arbitrary properties of a gaseous or liquid fluid medium, it being possible to detect one or multiple properties. The present invention is described below without limitation of further specific embodiments and applications, in particular with reference to sensor elements for detecting a gas, in particular an $H_2$ fraction in a measuring gas.

Sensor elements of the type described here find application in a number of areas, for example in automotive engineering, process engineering, chemistry, and mechanical engineering, in particular for determining gas concentrations. Thus, for example, determining hydrogen concentrations, for example in an air-hydrogen mixture, plays a major role in the application of hydrogen fuel cell systems. Safety-relevant applications are also to be mentioned. An air-hydrogen mixture having a hydrogen fraction of 4%, for example, is capable of ignition. Sensor elements for detecting hydrogen may be used in hydrogen fuel cell vehicles, for example, in order to detect hydrogen that occurs due to damage or defects, for example, and to trigger warning signals and/or protective measures by coupling to appropriate systems. Therefore, each fuel cell vehicle requires multiple hydrogen sensors, which either are mounted in the exhaust system or operate under atmospheric (ambient) conditions.

For these types of hydrogen sensors, numerous measurement principles may be relied on. These include the following measurement principles, among others: heat conduction, catalytic pellistor, electrochemical cell, semiconducting metal oxide, chemiresistor, field effect transistor.

Despite the advantages of the conventional sensor elements from the related art for detecting at least one property of a fluid medium, the potential for improvement still exists. For use in automotive engineering, such a hydrogen sensor must meet certain requirements. The above-mentioned measurement principles each have certain deficiencies or disadvantages with regard to these requirements. Thus, these types of sensor elements for the most part have an inadequate response time, a measuring range above the minimum measuring range, and/or a cross-sensitivity with respect to further components such as helium or volatile organic components. In addition, these sensor elements are sometimes based on costly electronic packaging.

SUMMARY

Within the scope of the present invention, a sensor for detecting at least one property of a fluid medium in a measuring chamber is provided which at least may largely avoid the disadvantages of conventional sensors for detecting at least one property of a fluid medium in a measuring chamber, and which provides sufficient sensitivity, measuring range, response time, and selectivity with regard to the requirements in automotive engineering.

A sensor according to an example embodiment of the present invention for detecting at least one property of a fluid medium in at least one measuring chamber, in particular for detecting an $H_2$ fraction in a measuring gas, includes at least:

a first sensor element that is designed to detect a heat conductivity of the fluid medium and to output a first measuring signal, a second sensor element that includes a semiconducting metal oxide and that is designed to output a second measuring signal, a third sensor element for detecting a physical property of the fluid medium, the third sensor element differing from the first sensor element and the second sensor element with regard to the detected physical property and being designed to output a third measuring signal, and an electronic evaluation unit for evaluating the first measuring signal, the second measuring signal, and the third measuring signal, the electronic evaluation unit being further designed to change operating parameters of the first sensor element, of the second sensor element, and/or of the third sensor element.

The information concerning the property of the fluid medium to be measured, for example an $H_2$ concentration in the supplied measuring gas, is generated primarily by the first sensor element in the form of a heat conductivity sensor element, and by the second sensor element in the form of a metal oxide (MOX) sensor element. The heat conductivity of a gas is inversely proportional to the square root of the mass of the gas molecules, so that gases with light atoms such as $H_2$ molecules or He atoms have a much higher heat conductivity than air, which is composed essentially of $N_2$ and $O_2$ molecules. The greater the fraction of light molecules, the higher is the measured heat conductivity. The MOX sensor element is made up of a semiconducting metal oxide such as $SnO_2$ or $WO_3$, whose electrical resistance decreases when a gas having a chemically reducing effect, for example hydrogen, methane, or water vapor, is contained in air. The content of reducing gases in air may thus be determined via the measured electrical resistance. However, the signals from the heat conductivity sensor element and the MOX sensor element are not unequivocally determined by the hydrogen concentration in air, since other gases in air may also give the same measuring result. This is referred to here as cross-sensitivity with regard to other gases, which limits the absolute sensor accuracy. To be able to ensure a sought accuracy of 0.1 vol % for $H_2$ for all possible air compositions, corrections in the signal processing are necessary, in that additional measured variables are detected and evaluated. Therefore, according to the present invention, at least one further sensor element for detecting a further physical property of the fluid medium is provided. For example, further sensor elements for the relative humidity, the gas temperature, and the gas pressure are integrated into the $H_2$ sensor, and their signals are taken into account in the electronic evaluation unit as a central electronic signal processing unit. However, this taking into account does not take place in the form of a family of characteristics, but instead it takes place by machine learning methods, for example by training a neural network.

According to an example embodiment of the present invention, the electronic evaluation unit may be designed to change operating parameters of the first sensor element, of the second sensor element, and/or of the third sensor element with the aid of an algorithm. The algorithm may in particular include an artificial neural network.

The training of the neural network takes place before the sensor is delivered. According to an example embodiment of the present invention, use is made of transfer learning methods in such a way that the entire time-consuming training of the neural network takes place at only a few product sensors. The remaining sensor products obtain these node parameters during their programming, and run through only a brief training for the purpose of individual fine tuning. The training lies in exposing the sensor in succession to air containing various fractions of gases, such as primarily $H_2$ or interfering gases such as He or $CH_4$, at various relative humidities and different air pressures and temperatures, and using the set parameters for the gas concentrations, relative humidity, air pressure, and temperature as training data for the neural network.

The third sensor element may be designed to detect at least one physical property selected from the group made up of: moisture, in particular relative humidity, pressure, in particular air pressure, and temperature, in particular air temperature.

It is explicitly emphasized that the sensor may include more than three sensor elements, for example four, five, or more sensor elements.

Within the scope of the complete training of the neural network, according to an example embodiment of the present invention an optimization of the operating parameters of the individual sensor elements takes place, so that the time until the measured value is present, and the error between the measured and the actual $H_2$ concentration in air, is minimal. According to the present invention, the temperature of the MOX element, which is typically heated for operation, or the temperature of the measuring element of the heat conductivity sensor element is selected here as a parameter to be trained.

The first sensor element, the second sensor element, and the third sensor element may be sensor elements that are separate from one another. Alternatively, the first sensor element, the second sensor element, and the third sensor element may be sensor elements that are integrated into a sensor chip.

Accordingly, the sensor elements do not necessarily have to be present as physically separate components that are connected by a circuit carrier. Sensor functions may also be integrated into a component or chip. Thus, for example, the sensor element for heat conductivity and the element containing MOX may be integrated into a chip or a module. Likewise, the sensor elements for humidity, pressure, and temperature may be integrated into a module or a chip. All possible aggregations of individual or multiple functions are preferably in one module.

The sensor may also include a voltage transformer. The voltage transformer may be designed for connection to an external voltage source. The voltage transformer may also be designed to generate a supply voltage for the first sensor element, the second sensor element, and the third sensor element.

The voltage transformer thus obtains the supply voltage for the overall sensor from the outside, and generates from same the supply voltages needed for the sensor elements.

The sensor may also include an interface, the interface being designed to receive control commands from an external control unit and/or to output measured data of the sensor to an external control unit. The interface is a data exchange module, for example. The data exchange receives control commands for the overall sensor from the outside, and outputs measured data concerning the hydrogen concentration and other requested measured data or metadata to the outside. Such a data exchange module is also known as a communication chip.

The sensor may also include a sensor housing. The first sensor element, the second sensor element, the third sensor element, and the electronic evaluation unit may be situated in the sensor housing. The sensor housing may include at least one opening with the aid of which the first sensor element, the second sensor element, and the third sensor element may be exposed to the fluid medium.

Via a gas-permeable opening in the sensor housing, the gas whose hydrogen concentration is to be measured is thus brought into the housing, where it is supplied to the sensor elements.

According to an example embodiment of the present invention, the electronic evaluation unit may be designed to output control signals and/or correction signals to the first sensor element, the second sensor element, and the third sensor element in order to change the operating parameters.

The sensor thus includes multiple sensor elements and a central electronic processing unit in a sensor housing, the central electronic processing unit processing the signals of the sensor elements using machine learning methods to ascertain therefrom a measured value for the present $H_2$ concentration within <1 s, with low error<0.1 vol % $H_2$, which is provided to the user via the output interface of the sensor. It is likewise provided that from the central electronic processing unit also control signals or correction signals are guided to the sensor elements within the scope of the signal processing in order to improve the overall sensor performance or to optimize the accuracy or response time.

Within the scope of the present invention, a sensor is basically understood to mean an arbitrary device that may detect the at least one property of the fluid medium, and that may generate, for example, at least one measuring signal corresponding to the detected property, for example an electrical measuring signal such as a voltage or a current. The measuring signal may be output by one or multiple sensor elements as components of the sensor. The property may be a physical and/or a chemical property, for example. In addition, combinations of properties may be detectable. In particular, the sensor may be designed to detect at least one property of a gas, in particular an $H_2$ fraction in a measuring gas. Other properties and/or combinations of properties may also be detectable.

The sensor may in particular be configured for use in a hydrogen fuel cell vehicle. The measuring chamber in principle may be an arbitrary open or closed chamber in which the fluid medium, in particular the measuring gas, is accommodated, and/or through which the fluid medium, in particular the measuring gas, flows.

Within the scope of the present invention, a housing is basically understood to mean an arbitrary component or a group of components that may completely or partially enclose and/or seal off the sensor element from the outside, and that may impart mechanical stability to the sensor element. In particular, a housing may enclose at least one interior space. For example, the housing may at least partially enclose the interior space and at least partially delimit it from its surroundings. The housing may in particular be completely or partially made of at least one of the following materials: plastic, metal, ceramic, or glass.

BRIEF DESCRIPTION OF THE DRAWINGS

Further optional particulars and features of the present invention result from the following description of preferred exemplary embodiments that are schematically illustrated in the figures.

DETAILED DESCRIPTION OF EXAMPLE EMBODIMENTS

Figure 1:
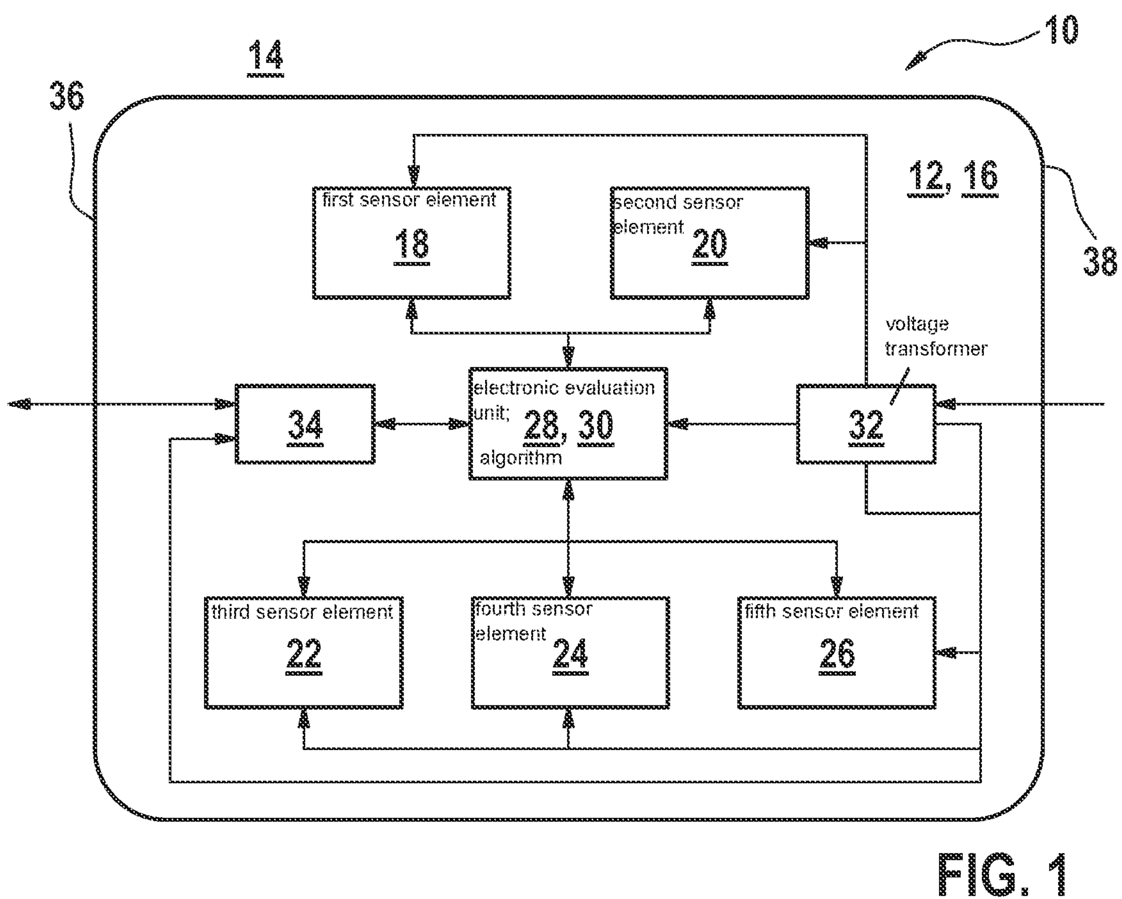
FIG. 1 shows a schematic illustration of a sensor according to an example embodiment of the present invention for detecting at least one property of a fluid medium in at least one measuring chamber.

FIG. 1 shows a schematic illustration of a sensor 10 according to an example embodiment of the present invention for detecting at least one property of a fluid medium 12 in at least one measuring chamber 14, in particular for detecting an $H_2$ fraction in a measuring gas 16. Sensor 10 may in particular be configured for use in a hydrogen fuel cell vehicle. However, other applications are also possible. Sensor 10 may in particular include one or multiple functional elements not illustrated in the figures, for example electrodes, electrode leads and contacts, multiple layers, or other elements. Correspondingly, sensor 10 may be mounted in the exhaust system of the hydrogen fuel cell vehicle or may operate under atmospheric (ambient) conditions. Therefore, the measuring chamber may be an exhaust system or an interior space of the hydrogen fuel cell vehicle.

Sensor 10 includes a first sensor element 18. First sensor element 18 is designed to detect a heat conductivity of fluid medium 12. First sensor element 18 is further designed to output a first measuring signal.

Sensor 10 also includes a second sensor element 20. Second sensor element 20 is a MOX sensor element. Second sensor element 20 thus includes a semiconducting metal oxide. Second sensor element 20 is also designed to output a second measuring signal.

Sensor 10 also includes a third sensor element 22. Third sensor element 22 is designed to detect a physical property of the fluid medium. Third sensor element 22 differs from first sensor element 18 and second sensor element 20 with regard to the detected physical property. In the specific embodiment shown, third sensor element 22 is designed to detect moisture of fluid medium 12. For example, third sensor element 22 is designed to detect a relative humidity. Third sensor element 22 is designed to output a third measuring signal.

In the specific example embodiment shown, sensor 10 includes more than three sensor elements. Thus, sensor 10 also includes a fourth sensor element 24. Fourth sensor element 24 is designed to detect a physical property of the fluid medium. Fourth sensor element 24 differs from first sensor element 18 and second sensor element 20 with regard to the detected physical property. In the specific embodiment shown, fourth sensor element 24 is designed to detect a temperature of fluid medium 12. For example, fourth sensor element 24 is designed to detect an air temperature. Fourth sensor element 24 is designed to output a fourth measuring signal.

Sensor 10 also includes a fifth sensor element 26. Fifth sensor element 26 is designed to detect a physical property of the fluid medium. Fifth sensor element 26 differs from first sensor element 18 and second sensor element 20 with regard to the detected physical property. In the specific embodiment shown, fifth sensor element 26 is designed to detect a pressure of fluid medium 12. For example, fifth sensor element 26 is designed to detect an air pressure. Fifth sensor element 26 is designed to output a fifth measuring signal.

Sensor elements 18, 20, 22, 24, 26 may be sensor elements that are separate from one another. Sensor elements 18, 20, 22, 24, 26 are preferably sensor elements that are integrated into a sensor chip or sensor module, not shown in greater detail.

Sensor 10 also includes an electronic evaluation unit 28. Electronic evaluation unit 28 is designed to evaluate the first measuring signal, the second measuring signal, and the third measuring signal. In addition, electronic evaluation unit 28 is designed to evaluate the fourth measuring signal and the fifth measuring signal. For this purpose, electronic evaluation unit 28 communicates with sensor elements 18, 20, 22, 24, 26. Electronic evaluation unit 28 is also designed to change operating parameters of first sensor element 18, of second sensor element 20, and/or of third sensor element 24. In addition, electronic evaluation unit 28 is designed to change operating parameters of fourth sensor element 24 and of fifth sensor element 26. Electronic evaluation unit 28 is designed to change operating parameters of first sensor element 18, of second sensor element 20, of third sensor element 22, of fourth sensor element 24, and of fifth sensor element 26 with the aid of an algorithm 30. Algorithm 30 includes an artificial neural network. Machine learning methods are reverted to for the artificial neural network. Electronic evaluation unit 28 is designed to output control signals and/or correction signals to sensor elements 18, 20, 22, 24, 26 in order to change or adapt their operating parameters.

Sensor 10 also includes a voltage transformer 32. Voltage transformer 32 is designed for connection to an external voltage source (not shown in greater detail). Voltage transformer 32 is also designed to generate a supply voltage for sensor elements 18, 20, 22, 24, 26. In other words, voltage transformer 32 supplies sensor elements 18, 20, 22, 24, 26 with the particular required supply voltage.

Sensor 10 also includes an interface 34. Interface 34 is designed to receive control commands from an external control unit (not shown in greater detail). Interface 34 is also designed to output measured data of sensor 10 to the external control unit. Correspondingly, interface 34 may be designed as a data exchange module.

Sensor 10 also includes a sensor housing 36. Sensor elements 18, 20, 22, 24, 26 and electronic evaluation unit 28 are situated in sensor housing 36. In addition, voltage transformer 32 and interface 34 are at least partially situated in sensor housing 36. Sensor housing 36 includes at least one opening 38. Sensor elements 18, 20, 22, 24, 26 may be exposed to the fluid medium and contacted by it with the aid of opening 38.

Figure 2:
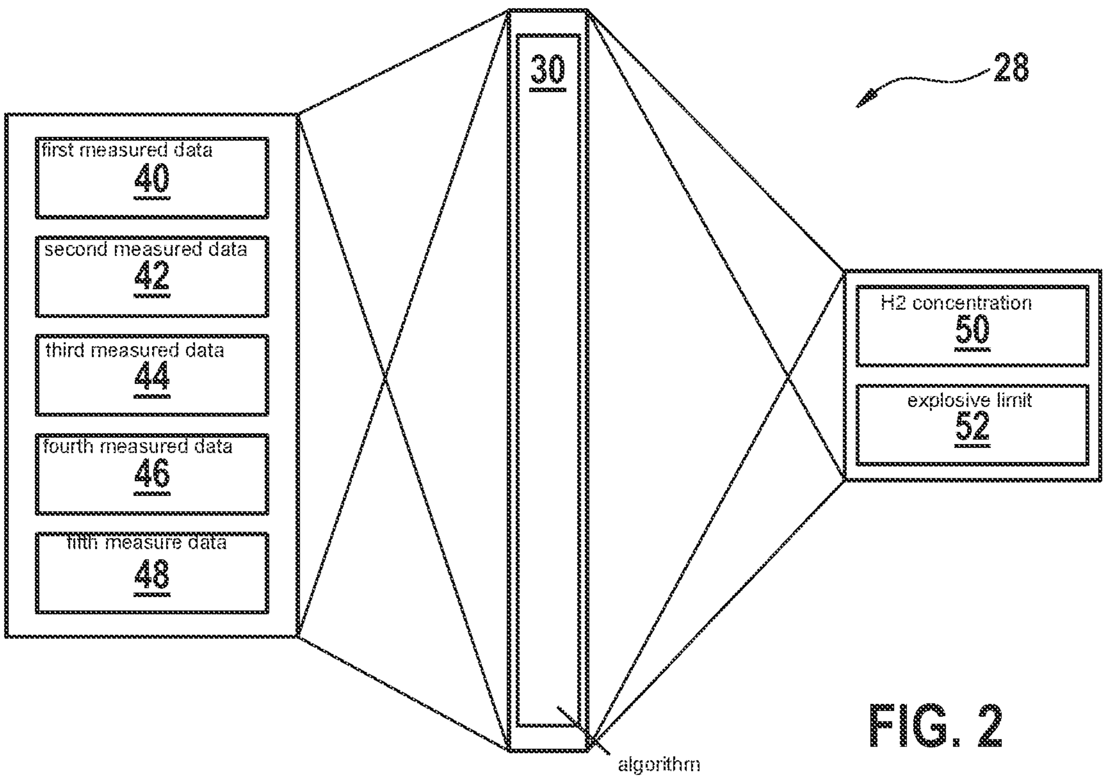
FIG. 2 shows a schematic illustration of the electronic evaluation unit, according to an example embodiment of the present invention.

FIG. 2 shows a schematic illustration of electronic evaluation unit 28. As mentioned above, an algorithm 30 that includes an artificial neural network runs in the electronic evaluation unit. FIG. 2 shows in particular a schematic illustration of algorithm 30. Algorithm 30 is supplied with first measured data 40 from first sensor element 18, second measured data 42 from second sensor element 20, third measured data 44 from third sensor element 22, fourth measured data 46 from fourth sensor element 24, and fifth measured data 48 from fifth sensor element 46. $H_2$ concentration 50 in vol %, for example, and the percentage of reaching explosive limit 52 in percent of $H_2$ in air are ascertained from measured data 40, 42, 44, 46, 48 with the aid of algorithm 30.

The operating method of sensor 10 is described below. In addition to sensor elements 18, 20, 22, 24, 26 and electronic evaluation unit 28 as a central electronic signal processing unit, voltage transformer 32 and interface 34 as a data exchange module are contained in sensor 10. Voltage transformer 32 obtains from the outside the supply voltage for entire sensor 10, and generates therefrom the supply voltage needed for sensor elements 18, 20, 22, 24, 26. Data exchange module 34 receives control commands for entire sensor 10 from the outside, and outputs measured data concerning the hydrogen concentration and other requested measured data or metadata to the outside. Via gas-permeable opening 38 in sensor housing 36, measuring gas 16 whose hydrogen concentration is to be measured is brought into sensor housing 36, where it is supplied to sensor elements 18, 20, 22, 24, 26.

The information concerning the $H_2$ concentration to be measured in supplied measuring gas 16 is generated primarily by first sensor element 18 as a heat conductivity sensor element, and by second sensor element 20 as a MOX sensor element. The heat conductivity of a gas is inversely proportional to the square root of the mass of the gas molecules, so that gases with light atoms such as $H_2$ molecules or He atoms have a much higher heat conductivity than air, which is composed essentially of $N_2$ and $O_2$ molecules. The greater the fraction of light molecules, the higher is the measured heat conductivity. Second sensor element 20 includes or is made up of a semiconducting metal oxide such as $SnO_2$ or $WO_3$, whose electrical resistance decreases when a gas having a chemically reducing effect, for example hydrogen, methane, or water vapor, is contained in air. The content of reducing gases in air may thus be determined via the measured electrical resistance. As described, the signals of first sensor element 18 and second sensor element 20 are not unequivocally determined by the hydrogen concentration in air, since other gases in air may also give the same measuring result. This is referred to here as cross-sensitivity with regard to other gases, which limits the absolute sensor accuracy. To be able to ensure a sought accuracy of 0.1 vol % for $H_2$ for all possible air compositions, corrections in the signal processing are necessary, in that additional measured variables are detected and evaluated. According to the present invention, sensor elements 22, 24, 26 for the relative humidity, the gas temperature, and the gas pressure, respectively, are integrated into the $H_2$ sensor, and their signals are taken into account in electronic evaluation unit 28. However, this taking into account does not take place in the form of a family of characteristics, but instead it takes place by machine learning methods, for example by training a neural network of algorithm 30, as schematically illustrated in FIG. 2. The training of the neural network takes place before sensor 10 is delivered. Use is made of transfer learning methods in such a way that the entire time-consuming training of the neural network takes place at only a few product sensors. The remaining sensor products obtain these node parameters during their programming, and run through only a brief training for the purpose of individual fine tuning. The training lies in exposing sensor 10 in succession to air containing various fractions of gases, such as primarily $H_2$ or interfering gases such as He or $CH_4$, at various relative humidities and different air pressures and temperatures, and using the set parameters for the gas concentrations, relative humidity, air pressure, and temperature as training data for the neural network.

Within the scope of the complete training of the neural network, according to the present invention an optimization of the operating parameters of individual sensor elements 18, 20, 22, 24, 26, takes place, so that the time until the measured value is present, and the error between the measured and the actual $H_2$ concentration in air, become minimal. According to the present invention, the temperature of second sensor element 20, which is typically heated for operation, or the temperature of first sensor element 18 is selected here as a parameter to be trained.

Sensor 10 according to the present invention is demonstrable by the presence of a sensor element for heat conductivity and a sensor element including semiconducting metal oxide, and at least one sensor element for some other physical variable, for example relative humidity, pressure, and temperature, as well as a central electronic signal processing unit. In addition, the present invention is recognizable by the product during operation in that the operating parameters for the sensor elements adapt to the external conditions, and thus always meet the requirements for the measuring accuracy for $H_2$ vol % and the response time. Circuit elements or circuit units that are optimized for the neural networks are recognizable in the central electronic signal processing unit.

What is claimed is:

1. A sensor for detecting at least one property of a fluid medium in at least one measuring chamber, including for detecting an $H_2$ fraction in a measuring gas, the sensor comprising:

a first sensor element configured to detect a heat conductivity of the fluid medium and to output a first measuring signal;

a second sensor element that includes a semiconducting metal oxide and that is configured to output a second measuring signal;

a third sensor element configured to detect a physical property of the fluid medium, the third sensor element differing from the first sensor element and the second sensor element with regard to the detected physical property and being configured to output a third measuring signal; and an electronic evaluation unit configured to evaluate the first measuring signal, the second measuring signal, and the third measuring signal, the electronic evaluation unit being further configured to change operating parameters of the first sensor element, and/or of the second sensor element, and/or of the third sensor element, wherein the electronic evaluation unit is configured to change, using an algorithm, the operating parameters of the first sensor element and/or of the second sensor element and/or of the third sensor element, wherein the algorithm includes an artificial neural network, wherein the electronic evaluation unit is configured to output correction signals to the first sensor element, the second sensor element, and the third sensor element, the correction signals causing changes in the operating parameters of the respective sensor elements.

2. The sensor as recited in claim 1, wherein the third sensor element is configured to detect at least one physical property selected from the group made up of: moisture, relative humidity, pressure, air pressure, temperature, air temperature.

3. The sensor as recited in claim 1, wherein the first sensor element, the second sensor element, and the third sensor element are sensor elements that are separate from one another.

4. The sensor as recited in claim 1, wherein the first sensor element, the second sensor element, and the third sensor element are sensor elements that are integrated into a sensor chip.

5. The sensor as recited in claim 1, further comprising a voltage transformer, the voltage transformer being configured for connection to an external voltage source, the voltage transformer also being configured to generate a supply voltage for the first sensor element, the second sensor element, and the third sensor element.

6. The sensor as recited in claim 1, further comprising an interface, the interface being configured to receive control commands from an external control unit and/or to output measured data of the sensor to an external control unit.

7. The sensor as recited in claim 1, further comprising a sensor housing, the first sensor element, the second sensor element, the third sensor element, and the electronic evaluation unit being situated in the sensor housing, the sensor housing including at least one opening using which the first sensor element, the second sensor element, and the third sensor element may be exposed to the fluid medium.

8. The sensor as recited in claim 1, wherein the electronic evaluation unit is configured to output control signals to the first sensor element, the second sensor element, and the third sensor element to change the operating parameters.

* * * * *